US011774736B2

(12) United States Patent
Forster

(10) Patent No.: US 11,774,736 B2
(45) Date of Patent: Oct. 3, 2023

(54) FILTER SWITCHING DEVICE FOR AN OPTICAL OBSERVATION INSTRUMENT WITH TWO OPTICAL PATHS, OPTICAL OBSERVATION INSTRUMENT AND METHOD FOR SWITCHING A FILTER OF AN OPTICAL OBSERVATION INSTRUMENT

(71) Applicant: KARL STORZ SE & Co. KG, Tuttlingen (DE)

(72) Inventor: Jonas Forster, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 304 days.

(21) Appl. No.: 17/145,470

(22) Filed: Jan. 11, 2021

(65) Prior Publication Data
US 2021/0215920 A1      Jul. 15, 2021

(30) Foreign Application Priority Data
Jan. 14, 2020  (DE) ................. 10 2020 100 676.4

(51) Int. Cl.
*G02B 21/00* (2006.01)
*G02B 21/22* (2006.01)

(52) U.S. Cl.
CPC ..... *G02B 21/0044* (2013.01); *G02B 21/0092* (2013.01); *G02B 21/22* (2013.01)

(58) Field of Classification Search
CPC ........... G02B 21/0044; G02B 21/0092; G02B 21/22; G02B 7/006; G02B 21/16;
(Continued)

(56) References Cited

U.S. PATENT DOCUMENTS 4,168,904 A * 9/1979 Furukawa ............... G03B 27/73
355/71
5,162,647 A * 11/1992 Field, Jr. ................ H01J 29/898
348/270
(Continued)

FOREIGN PATENT DOCUMENTS

CN      106200213 B  *  1/2019  ............ G02B 7/006
CN      106200213 B      1/2019
(Continued)

OTHER PUBLICATIONS

Extended European Search Report for corresponding European Application No. 21150897.3, dated Jun. 22, 2021.
(Continued)

*Primary Examiner* — Mustak Choudhury
(74) *Attorney, Agent, or Firm* — Jason H. Vick; Sheridan Ross, PC

(57) ABSTRACT

The invention relates to a filter interchange apparatus for an optical observation instrument having two beam paths, in particular for a stereoscopic observation instrument, in particular for a stereo video endoscope, a stereo exoscope or a stereo surgical microscope, wherein the filter interchange apparatus comprises a first filter wheel, a second filter wheel and a third filter wheel, wherein the filter wheels are arranged in succession along a common axle and are rotatable about the common axle and relative to one another. Each filter wheel comprises at least one filter and at least one free optical passage such that a filter or a free optical passage of each filter wheel is introducible into each of the two beam paths. The second filter wheel is drivable and the first filter wheel is coupled to the second filter wheel via a first entrainment element and the third filter wheel is coupled to the second filter wheel via a second entrainment element. Moreover, the invention relates to an optical observation instrument having two beam paths, in particular a stereo
(Continued)

video endoscope, a stereo exoscope or a stereo surgical microscope, and to a method for changing a filter of an optical observation instrument.

19 Claims, 9 Drawing Sheets

(58) Field of Classification Search
CPC .............. G02B 26/008; G02B 21/248; G02B 21/0012; G02B 23/2407; A61B 1/00186
See application file for complete search history.

(56) References Cited

U.S. PATENT DOCUMENTS

| | | | |
|---|---|---|---|
| 5,852,519 A * | 12/1998 | Do | G02B 7/00 359/822 |
| 7,133,198 B2 | 11/2006 | Schnitzler et al. | |
| 10,571,309 B2 * | 2/2020 | Grau | G01J 4/04 |
| 2001/0055150 A1 | 12/2001 | Ito | |
| 2004/0017607 A1 | 1/2004 | Hauger et al. | |
| 2005/0111090 A1 * | 5/2005 | Kleinteich | G02B 21/16 359/368 |
| 2006/0132779 A1 * | 6/2006 | Hunt | G01N 21/359 356/418 |
| 2010/0110538 A1 | 5/2010 | Steffen et al. | |
| 2011/0134518 A1 | 6/2011 | Doi et al. | |
| 2011/0299174 A1 * | 12/2011 | Obrebski | G02B 21/22 359/672 |
| 2012/0243079 A1 | 9/2012 | Böhm et al. | |
| 2012/0265023 A1 | 10/2012 | Berci et al. | |
| 2013/0140411 A1 | 6/2013 | Frick | |
| 2014/0347461 A1 * | 11/2014 | Kleppe | G02B 21/361 348/79 |
| 2015/0085084 A1 | 3/2015 | Heni et al. | |
| 2016/0286197 A1 | 9/2016 | Schwarz et al. | |
| 2017/0146780 A1 | 5/2017 | Nakamura | |
| 2018/0164568 A1 | 6/2018 | Kubek | |
| 2019/0079248 A1 * | 3/2019 | Hagen | G02B 6/08 |

FOREIGN PATENT DOCUMENTS

| | | |
|---|---|---|
| DE | 10130119 A1 | 1/2002 |
| DE | 10336890 A1 | 3/2005 |
| DE | 102006004232 A1 | 8/2007 |
| DE | 102009011681 A | 8/2010 |
| DE | 102009019575 A1 | 11/2010 |
| DE | 202011000688 U1 | 6/2011 |
| DE | 102011054031 A1 | 10/2012 |
| DE | 102013110543 A1 | 3/2015 |
| EP | 1333305 B1 | 8/2003 |
| EP | 1538471 A1 | 6/2005 |
| EP | 1333305 B1 | 4/2007 |
| EP | 2514357 A1 | 10/2012 |
| EP | 3073307 A1 | 9/2016 |
| EP | 3178434 A1 | 6/2017 |
| EP | 3197146 A1 | 7/2017 |
| EP | 3514595 A1 | 7/2019 |
| WO | WO 2015/016166 A1 | 2/2015 |
| WO | WO 2019/120553 A1 | 6/2019 |
| WO | WO 2019/181149 A1 | 9/2019 |

OTHER PUBLICATIONS

Extended European Search Report for corresponding European Application No. 21150921.1, dated Jun. 10, 2021.
U.S. Appl. No. 17/145,495, filed Jan. 11, 2021.
Image of an Arriscope Instrument—Date Unknown.
Screenshot of an Image of an Arriscope Instrument—Date Unknown.
Office Action for corresponding German Application No. 102020100676.4, dated Aug. 31, 2020.
Office Action for corresponding German Patent Application No. 102020100674.8, dated Aug. 28, 2020.
Office Action for U.S. Appl. No. 17/145,495, dated Dec. 21, 2022.
Office Action for U.S. Appl. No. 17/145,495, dated Jul. 3, 2023.

* cited by examiner

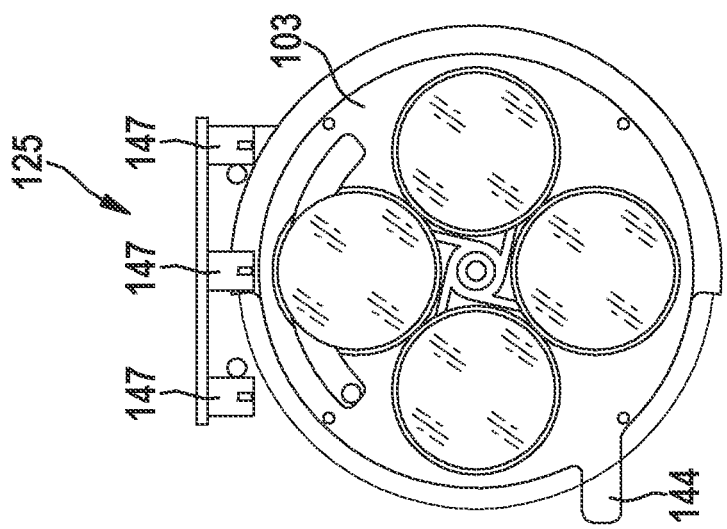
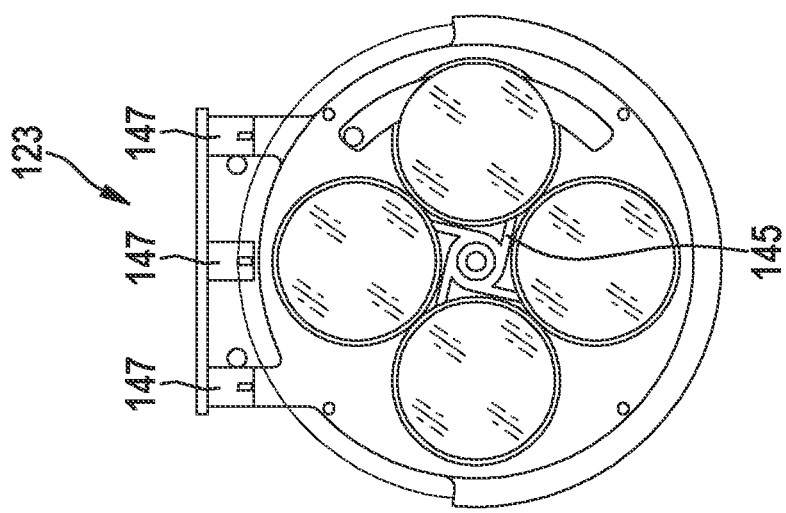
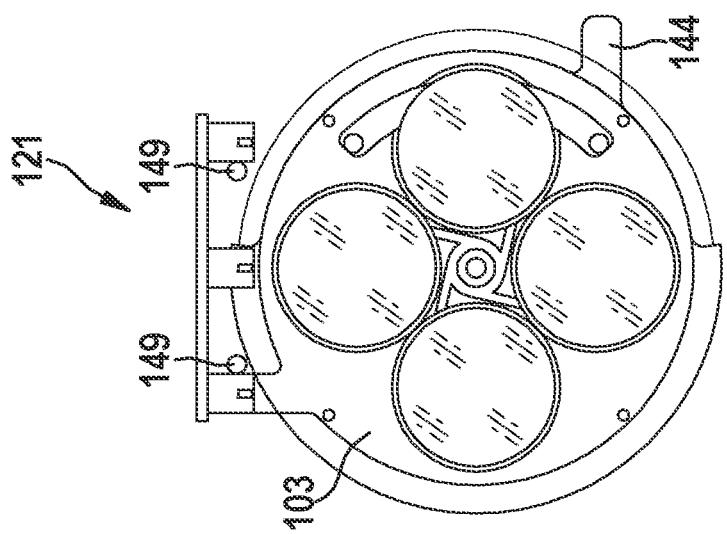
Fig. 8

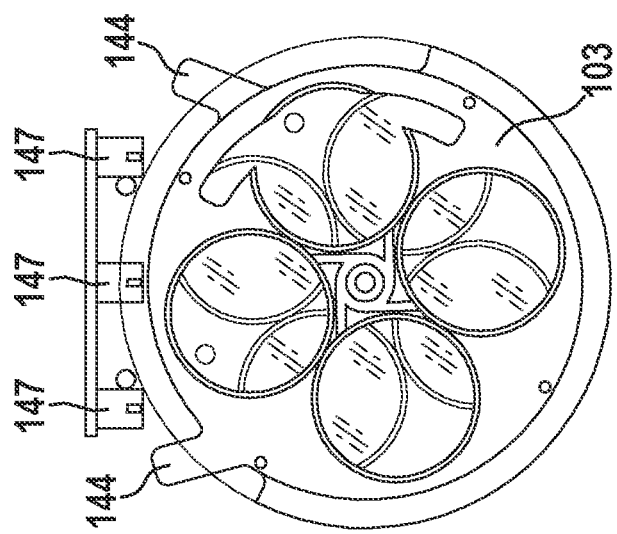
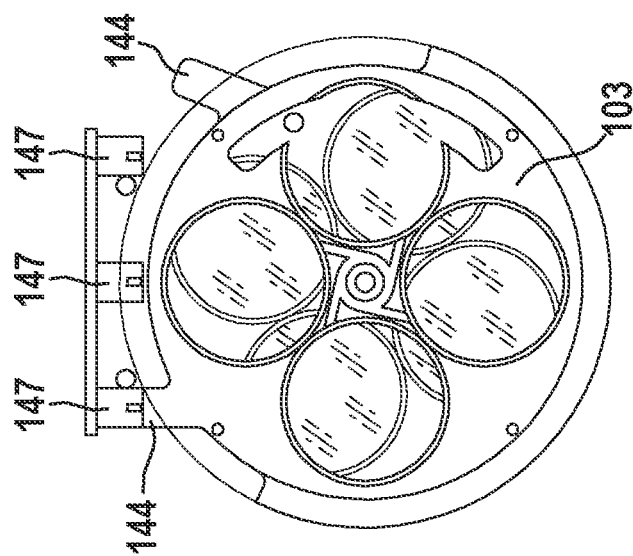
Fig. 9

FILTER SWITCHING DEVICE FOR AN OPTICAL OBSERVATION INSTRUMENT WITH TWO OPTICAL PATHS, OPTICAL OBSERVATION INSTRUMENT AND METHOD FOR SWITCHING A FILTER OF AN OPTICAL OBSERVATION INSTRUMENT

CROSS-REFERENCE TO RELATED APPLICATIONS

This application claims the benefit under 35 U.S.C. 119(a) to German Patent Application No. 10 2020 100 676.4, filed Jan. 14, 2020, the disclosure of which is incorporated herein by reference in its entirety

SUMMARY

The present invention relates to a filter interchange apparatus for an optical observation instrument having two beam paths, in particular for a stereoscopic observation instrument, for instance a stereo video endoscope, a stereo exoscope or a stereo surgical microscope. Further, the invention relates to such an optical observation instrument and to a method for changing a filter of an optical observation instrument having two beam paths.

To observe an operating field during a surgical intervention on a human or animal body, optical observation instruments have been disclosed, which provide a surgeon and, possibly, further persons with an accurate or magnified observation of the operating field or an object field on the body. Such optical observation instruments can be embodied, for example, as a surgical microscope or as an exoscope. Likewise, optical observation instruments embodied as endoscopes for observing an object field in a body-internal cavity are known.

A spatial perception of the object field is helpful to the operating surgeon when carrying out a surgical operation. Facilitating an improved spatial perception of the object field by way of stereoscopic optics, in which two images of the object field are recorded from slightly different perspectives, is known. The two images which, together, represent the stereoscopic image are also referred to as "half images" or as "stereo half images". The two half images are separately presented to the right and the left eye of the surgeon, and so the latter can obtain a spatial impression of the object field. For example, a monitor suitable for a stereoscopic display can be provided for this, for instance a screen with alternating polarization, with the surgeon wearing polarization glasses with different polarizations of the two lenses.

Further, the capability of introducing different filters into one or more beam paths of an optical observation instrument for the purposes of improving the image quality or for different observation modes is known. In particular, for fluorescence detection purposes, it is known to radiate fluorescence excitation radiation at a tissue to be examined and to observe the fluorescence radiation subsequently emitted by the tissue, said fluorescence radiation, as a rule, being located at longer wavelengths than the fluorescence excitation radiation that has been radiated in. In so doing, it is possible to observe both the autofluorescence of the tissue and the fluorescence emission of fluorescent dyes or photosensitizers supplied to the body in advance in a targeted manner. Since fluorescence excitation radiation, which is typically significantly brighter than the fluorescence radiation, is also radiated back by the tissue, it is necessary to block the back-scattered fluorescence excitation radiation, for the purposes of which a suitable filter depending on the fluorescence mode must be introduced into an observation beam path.

Observing the fluorescence radiation facilitates an improved distinction between tissue types or an improved identification of diseased tissue, wherein respectively appropriate different photosensitizers are advantageous for different tissues. By way of example in order to be able to distinguish in a differentiated manner between vital and necrotic tumor tissue, normal tissue and blood vessels and to determine the activity of the respective tissue types and/or cells, it is desirable, in particular, to be able to observe three different fluorescence modes, for the purposes of which three spectrally different, changeable filters are necessary.

DE 20 2011 000 688 U1 has disclosed an apparatus for receiving filters for microscopes, which has two filter wheels that are independently rotatable about the same axis of rotation, wherein the two filter wheels are offset relative to one another when seen along the axial direction of the axis of rotation. The apparatus comprises a drive unit for rotating the first filter wheel and for rotating the second filter wheel about the axis of rotation. Both filter wheels each comprise a multiplicity of receiving regions for receiving, in each case, at least one filter and a pass region for the unfiltered passage of light. The apparatus may comprise a third filter wheel, which is likewise rotatable about the axis of rotation in a manner independent of the other two filter wheels. This apparatus is not suitable for a stereoscopic observation instrument.

EP 3 197 146 A1 has disclosed a medical observation appliance, in which a plurality of filters are arranged on the outer circumferential face of a swivelable holding frame which is rotatable about an axis of rotation that is perpendicular to the direction of an optical axis. A disadvantage here is that the holding frame requires much space outside of the vertical plane during the rotation.

According to EP 3 073 307 A1, an apparatus for recording an image of an object field on a human or animal body from outside of the body comprises an observation optical unit for recording the image of the object field, which comprises a first and a second stereo channel and which is rotatable about an axis of rotation that is at least approximately parallel to a viewing direction of the observation optical unit. The observation optical unit comprises a first filter, which can be swiveled into and out of a beam path of the first stereo channel, and a second filter, which can be swiveled into and out of a beam path of the second stereo channel. The first and the second filter are arranged on a common filter carrier that is swivelable perpendicular to the axis of rotation or the first and second filter are each received in a filter carrier, wherein a filter shaft of the filter carrier of the second stereo channel is driven via a gear by the filter shaft of the filter carrier of the first stereo channel.

It is an object of the present invention to improve the prior art. In particular, it is an object of the invention to specify a filter interchange apparatus for an optical observation instrument having two beam paths, in particular for a stereoscopic observation instrument such as a stereo video endoscope, a stereo exoscope or a stereo surgical microscope, which filter interchange apparatus facilitates the interchange of three different filters and requires less space. Further, it is an object of the invention to specify a corresponding optical observation instrument having two beam paths and an improved method for changing a filter of an optical observation instrument having two beam paths.

This object is achieved by a filter interchange apparatus as described herein.

Advantageous developments of the invention emerge from the dependent claims.

A filter interchange apparatus according to the invention for an optical observation instrument having two beam paths is embodied, in particular, as a filter interchange apparatus for a stereoscopic observation instrument, for example for a stereo video endoscope, a stereo exoscope or a stereo surgical microscope. By way of example, the stereoscopic observation instrument can comprise two image sensors for a stereoscopic fluorescence observation and two image sensors for a stereoscopic white light observation. In particular, the filter interchange apparatus is an apparatus which facilitates an interchange of one or more filters respectively situated in the beam path, in particular an interchange of observation filters. In so doing, the filter interchange apparatus is preferably embodied to alternately introduce filters with three different spectral filter characteristics into the beam paths and remove said filters therefrom again. Here, in particular, the two beam paths are the beam paths of the two stereo channels of the stereoscopic observation instrument or of the stereo video endoscope, of the stereo exoscope or of the stereo surgical microscope. The beam paths preferably extend parallel to one another, particularly in the region of the filter interchange apparatus; however, they can also form an angle with one another. By way of example, the beam paths can be afocal in the region of the filter interchange apparatus.

According to the invention, the filter interchange apparatus comprises a first filter wheel, a second filter wheel and a third filter wheel, wherein the filter wheels are arranged in succession along a common axle, are offset in the axial direction in particular and are for example flush with one another. The labels "first", "second" and "third" filter wheel only serve here to distinguish the filter wheels from one another and should not be construed as restrictive in respect of the arrangement of the filter wheels; in particular, this does not necessarily denote a sequence of the filter wheels in the beam paths. By way of example, the first, the second or the third filter wheel can be arranged first in the beam paths and the other two filter wheels can follow in different sequences. The first, the second and the third filter wheel are rotatable about the common axle and relative to one another in each case. In particular, the first, the second and the third filter wheel are rotatable about a respective axis of rotation, wherein the axes of rotation of the filter wheels are at least approximately flush with the common axle.

The common axle is preferably arranged or arrangeable in the optical observation instrument in such a way that it extends substantially parallel with the two beam paths and/or represents a center axis between the two beam paths. In particular, the common axle is formed by a machine element for bearing the rotatable filter wheels, which machine element need not rotate itself and transmits no torque. Consequently, such a fixed axle can also form a common axis of rotation of the filter wheels. In particular, a flush arrangement of the filter wheels in succession along the common axle can also be ensured by way of the common axle. To this end, each filter wheel has a central bore, for example, wherein the common axle is guided through these central bores of the filter wheels and hence the filter wheels lie flush along a straight line with their respective axes of rotation. By way of example, each filter wheel can be rotatably mounted by means of a plain, antifriction or ball bearing. The filter wheels can have different diameters and/or shapes on the outer circumference of each filter wheel. By way of example, one or more filter wheels can be embodied with an approximately circular or non-circular circumference, or else as interrupted filter holders.

The first, the second and the third filter wheel each comprise at least one filter and at least one free optical passage, wherein a filter or a free optical passage of each filter wheel is introducible into each of the two beam paths. In particular, the filters and the free optical passages are arranged in the filter wheels and the filter wheels are rotatable relative to one another in such a way that a filter or a free optical passage of the first filter wheel and, at the same time, a filter or a free optical passage of the second filter wheel and, furthermore, a filter or a free optical passage of the third filter wheel is introducible into the first of the two beam paths, with not all combinations of the filters and free optical passages of the three filter wheels necessarily having to be realizable. A corresponding statement applies to the second of the two beam paths. Preferably, the filters and the free optical passages are arranged and the filter wheels are rotatable in such a way that two of the same types of filter are introducible opposite one another into the two beam paths in each case, and are removable therefrom again.

In particular, such a filter is embodied to select incident radiation according to the wavelength in the optical wavelength range or in adjacent wavelength ranges and to allow a portion to pass through while another portion is blocked. In particular, "the same types of filter" is understood to mean that the same types of filter carry out the same selection of incident radiation, for example have the same spectral filter characteristics. Here, a "free optical passage" is understood to mean an optical element and/or a region of the respective filter wheel which allows radiation to pass without a selection, in particular without a spectral selection. Therefore, a free optical passage can, for example, be a passage opening or else a spectrally non-selective optical element.

By way of example, each filter wheel can be embodied as a disk, wherein one or more filters and one or more free passages can be arranged at a uniform distance from one another and at the same distance from the respective or common axis of rotation. By way of example, a filter wheel can have two filters and two free passages, which are arranged opposite one another and with an offset of 90° from one another in each case. The filters and the free passages are able to be screwed or slotted into the filter wheel, in particular, and preferably have a form and dimension which approximately corresponds to a respective cross section of the two beam paths, and said filters and free passages each have a circular embodiment, for example. The filters and the free optical passages have a specified filter position on the filter wheel in particular.

According to the invention, one of the filter wheels is drivable; in particular, only one of the filter wheels is drivable, for example by means of a drive. In the present application, the drivable filter wheel is referred to as the "second" filter wheel; the latter can be arranged upstream, between or downstream of the first and the third filter wheel in the beam paths. Consequently, only the second filter wheel, in particular, is drivable by means of the drive, said drive not engaging with the first and the third filter wheel. Further according to the invention, the first filter wheel is coupled to the second filter wheel via a first entrainment element and the third filter wheel is coupled to the second filter wheel via a second entrainment element. In particular, the entrainment element is a component which, when moved, likewise puts another filter wheel into rotational movement and consequently entrains the latter or, depending on the direction of rotation and position of the filter wheels, leaves the latter standing. In particular, the first filter wheel is coupled to the second filter wheel via the entrainment element in such a way that, when the second filter wheel rotates, the first filter wheel is able to be entrained by means of the entrainment element and consequently likewise rotates in the direction of rotation of the second filter wheel, or else is able to freewheel and hence left standing; accordingly, the third filter wheel is coupled to the second filter wheel, in particular by way of the entrainment element, in such a way that, when the second filter wheel rotates in a direction of rotation, the third filter wheel is able to be entrained or able to freewheel by means of the entrainment element.

Consequently, a filter interchange apparatus is provided in which, as a result of an optimal arrangement and movement connection of three filter wheels, at least three different filter types, in particular filters with three different spectral filter characteristics, are able to be inserted into the beam paths while little installation space is required. It is particularly advantageous that the filter interchange apparatus in this case substantially only takes up an installation space that would also be claimed by a single filter wheel. In particular, what is able to be realized as a result of three filter wheels being successively arranged flush in the beam direction is a change of three different filters in the two beam paths, wherein the filter wheels each have an external diameter that equals or is only slightly larger than twice the diameter of each filter, and consequently this also allows the filter interchange apparatus to be configured in a particularly compact fashion.

Moreover, a quick change of the filters is able to be realized in the filter interchange apparatus since the filter wheels already lie transversely to the direction of the beam paths and only need to be rotated in order to introduce the respective desired filter into the beam path. This facilitates a simultaneous or virtually simultaneous pictorial representation of different recorded types of fluorescence and/or white light images.

Furthermore, a particularly simple construction is facilitated as a result of three filter wheels which are passed by the two beam paths being arranged coaxially in succession, wherein only one of the filter wheels is drivable, which is referred to here as second filter wheel and which can impress a rotation upon the first filter wheel and/or the third filter wheel by way of its entrainment element in order to insert appropriate filters. In particular, only a single drive is necessary and merely the second filter wheel must be configured to allow the drive to engage thereon. This may also render achievable a particularly space-saving arrangement.

According to a preferred embodiment of the invention, the drivable filter wheel, i.e., the second filter wheel, is arranged between the first and the third filter wheel, for example approximately centrally between the first and third filter wheel as seen along the common axle. As a result of only the middle filter wheel being drivable and the filter wheel arranged upstream and downstream thereof being coupled therewith by way of the first or the second entrainment element, a particularly simple arrangement and configuration of the filter wheels is achievable, which facilitates a particularly reliable and precise filter change.

Preferably, the first filter wheel is coupled to the second filter wheel via the first entrainment element in such a way that, proceeding from an initial position, the first filter wheel is entrained in the case of a rotation of the second filter wheel in a first direction of rotation of the second filter wheel and left standing in the case of a rotation of the second filter wheel in a second direction of rotation, which is opposite to the first. Consequently, the first filter wheel is entrained by the second or not depending on a direction of rotation of the second filter wheel and an initial rotational position of the first and the second filter wheel, in particular a relative initial position of the first filter wheel in relation to the second.

By preference, the third filter wheel is coupled to the second filter wheel via the second entrainment element in such a way that, proceeding from an initial position, the third filter wheel is left standing in the case of a rotation of the second filter wheel in a first direction of rotation of the second filter wheel and entrained in the case of a rotation of the second filter wheel in a second direction of rotation, which is opposite to the first. Consequently, the first filter wheel is entrained by the second or not depending on a direction of rotation of the second filter wheel and an initial rotational position of the second and the third filter wheel, in particular a relative initial position of the third filter wheel in relation to the second.

Particularly preferably, the first filter wheel is coupled to the second filter wheel via the first entrainment element in such a way that, proceeding from an initial position, the first filter wheel is entrained in the case of a rotation of the second filter wheel in a first direction of rotation of the second filter wheel and left standing in a second direction of rotation, which is opposite to the first, and, at the same time, the third filter wheel is coupled to the second filter wheel via the second entrainment element in such a way that, proceeding from an initial position, the third filter wheel is entrained in the case of a rotation of the second filter wheel in the second direction of rotation and is left standing in the first direction of rotation.

As a result, this can achieve an adjustment of the first, second and/or third filter wheel with respect to one another in a particularly simple fashion and hence a swiveling of the corresponding filters into the two beam paths by rotating the second filter wheel in the first or the second direction of rotation.

According to a preferred embodiment of the invention, the first entrainment element is embodied as an entrainment pin, which is arranged on the second filter wheel and which engages in a cutout of the first filter wheel and/or, the second entrainment element is embodied as an entrainment pin, which is arranged on the second filter wheel and which engages in a cutout of the third filter wheel, wherein the first or second entrainment element is able to freewheel within a respective freewheel angle range within the respective cutout. The entrainment pin is, in particular, a pin-shaped, cylindrical or conical component, which engages in a respective cutout and which is guided in movable fashion in the latter. Consequently, entrainment and consequently a rotational movement of the first filter wheel and/or of the third filter wheel can be realized directly by engagement of the respective entrainment pin in a cutout of the first filter wheel and/or of the third filter wheel. Preferably, the free wheel angle ranges of the first and the second entrainment element are approximately the same and equal approximately 90°, for example. Consequently, the length of the cutout within which the entrainment element is movable can correspond to an angular range of 90°, for example. In the case where the first and the third filter wheel are situated on the same side of the second filter wheel and, for example, the first filter wheel is arranged between the second and the third, the second entrainment element for entraining the third filter wheel can engage through an appropriately configured cutout of the first filter wheel or else, for example, engage around the first filter wheel around an outer circumference thereof.

What can be achieved in a particularly simple fashion as a result thereof is that the first filter wheel is entrained proceeding from an initial position in the case of a rotation of the second filter wheel in the first direction of rotation and left standing up to a freewheeling angle of 90°, for example, in the case of a rotation of the second filter wheel in the second, opposite direction of rotation. What can be achieved accordingly as a result thereof is that the third filter wheel is entrained proceeding from an initial position in the case of a rotation of the second filter wheel in the second direction of rotation and left standing up to the freewheeling angle in the case of a rotation of the second filter wheel in the first direction of rotation. Consequently, in order to set the desired filter swivel positions without separate drives being required for each filter wheel, the first filter wheel and/or the third filter wheel can be entrained or left standing purely by driving the second filter wheel. As a result, a very small installation space of the filter interchange apparatus is realizable.

The first and the second entrainment element can be securely arranged on the second filter wheel. The first and the second entrainment element can be embodied as one piece, in particular as a pin engaging through the disk of the second filter wheel and engaging in the cutout of the first filter wheel at one end and engaging in the cutout of the third filter wheel at the other end. Preferably, the second filter wheel has two separate entrainment pins, which protrude on a respective side of the second filter wheel and which respectively engage in the cutouts of the first filter wheel and of the third filter wheel.

Accordingly, provision can be made for the first entrainment element to be arranged on the first filter wheel and to engage in a cutout of the second filter wheel and/or for the second engagement element to be arranged on the third filter wheel and to engage in a cutout of the second filter wheel, which likewise renders it possible to obtain the first and/or the third filter wheel being entrained or left standing by the second filter wheel in the manner described above.

The cutout of the first and/or the third filter wheel is respectively embodied, in particular, as a ring segment-shaped groove or as a ring segment-shaped slot in a disk which forms the respective filter wheel. To the extent that a cutout is provided in the second filter wheel it can likewise be embodied as a ring segment-shaped groove or ring segment-shaped slot and, likewise, in the case where two cutouts are provided in the second filter wheel these can each be formed by ring segment-shaped grooves or slots. The respective groove or the respective slot extends, in particular, at a constant radius in a disk of the respective filter wheel, as seen from the common axle, and through an angle that approximately corresponds to the freewheel angle or which is so much larger that the entrainment element can freely move through the freewheel angle in the groove or in the slot. Preferably, the groove or the slot has a length corresponding to a circumference of a quarter circle about the common axis of rotation and consequently extends over an angular range of approximately 90°.

In particular, the cutout is arranged on the respective filter wheel in such a way that said cutout does not impair the optical properties of the filters. Preferably, the groove or the slot in the disk of a respective filter wheel extends through a free passage of the filter wheel. In this way, a particularly simple and compact structure for rotating the first and the third filter wheel can be achievable, without impairing the optical function of the filters.

To facilitate a return of the first and/or of the second filter wheel after a rotation of the first and/or the third filter wheel by entrainment by means of the first or the second entrainment element and, in particular, in order to reset the first and/or the third filter wheel in its respective initial rotary position, the first filter wheel and/or the third filter wheel comprise or comprises a restoring device. Here, the restoring device is, in particular, a machine element which is embodied to exert a torque on the first filter wheel or the third filter wheel in the direction of its respective initial position such that the first or the third filter wheel, when freed from entrainment, is restored to the respective initial position. By way of example, the restoring device can be a restoring spring, which is supported in spring-loaded state both on a stationary axle or a stationary holder and on a surface of the first filter wheel and/or of the third filter wheel. This can particularly easily facilitate a rotation of the first and/or of the third filter wheel in a freewheeling angle range independently of entrainment and consequently a rotation of the second filter wheel, and hence a setting of corresponding filter swivel positions.

According to a preferred embodiment of the invention, the first, the second and/or the third filter wheel each have two filters with a first, second and third filter characteristic, respectively, and each have two free optical passages. Consequently, the first filter wheel comprises two filters with a first filter characteristic and two free optical passages and/or the second filter wheel comprises two filters with a second filter characteristic and two free optical passages and/or the third filter wheel comprises two filters with a third filter characteristic and two free optical passages. Particularly preferably, the first, the second and the third filter wheel each have two filters with a first, second and third filter characteristic, respectively, and each have two free optical passages. Consequently, each filter wheel preferably has two filters, each of the same type, and two free optical passages. As a result of a filter wheel or each filter wheel respectively having exactly two filters of the same type, a quick and precise change of the filters is realizable, wherein a filter of the same type can be introduced into both beam paths.

According to a particularly preferred embodiment of the invention, the first, the second and/or the third filter wheel each have two filters with a first, second and third filter characteristic, respectively, which are arranged lying opposite one another and each have two free optical passages likewise arranged lying opposite one another. Consequently, the first filter wheel comprises two filters with a first filter characteristic lying opposite one another and two free optical passages lying opposite one another and/or the second filter wheel comprises two filters with a second filter characteristic lying opposite one another and two free optical passages lying opposite one another and/or the third filter wheel comprises two filters with a third filter characteristic lying opposite one another and two free optical passages lying opposite one another. Particularly preferably, the first, the second and the third filter wheel each have two filters with a first, second and third filter characteristic, respectively, which are arranged lying opposite one another and each have two free optical passages which are arranged lying opposite one another. Consequently, each filter wheel preferably has two filters, each of the same type lying opposite one another, and two free optical passages lying opposite one another. The opposition of the filters or of the free optical passages in this case respectively relates to the axis of rotation of the relevant filter wheel or to the common axle. As a result of a filter wheel or each filter wheel respectively having exactly two filters of the same type lying opposite one another, a particularly quick and precise change of the filters is realizable, wherein a filter of the same type can be introduced into both beam paths.

Alternatively, provision can be made in the case of one or more filter wheels for respectively two filters, in particular two filters of the same type, to be arranged next to one another and for two passages to be arranged next to one another, wherein the two filters are simultaneously introducible into the two beam paths or the two passages are simultaneously introducible into the two beam paths. By way of example, if both filters are arranged in an upper half of a filter wheel, these can respectively lie in a beam path in a first rotational position and can each lie outside of the beam paths in a second rotational position of the filter wheel which is rotated through 180°, wherein the two beam paths each extend through a free passage in the second rotational position. In this case, there would be a rotation or entrainment of a filter wheel through 180° or a freewheel angle of 180° for a filter change.

In a further embodiment, provision can be made for at least two different filter wheels to each have a filter of the same type, wherein the two filters of the same type and, in each case, a free optical passage of the two filter wheels are arrangeable with respect to one another in such a way that the two filters of the same type and the respective free optical passages are introducible lying opposite one another in the two beam paths. This can also allow the two beam paths to pass through the same type of filter.

In particular, the first, the second and the third filter characteristic are embodied for spectral selection of the incident radiation, wherein the first, the second and the third filter characteristic are preferably different spectral filter characteristics.

To facilitate the observation and/or the image recording in different fluorescence modes, one or more of the filters is or are embodied as fluorescence filters. In particular, the filters with the first, second and/or third filter characteristic are embodied as fluorescence filters, particularly preferably the filters with the first, second and third filter characteristic are each fluorescence filters. A fluorescence filter has, in particular, such a filter characteristic that, for a respective fluorescence mode, radiation in the wavelength range of the respective specific fluorescence excitation radiation is at least largely blocked and there is at least substantial passing in the wavelength range of the respective specific fluorescence emission radiation. For instance, such a filter can be a bandpass filter, a notch filter, an edge filter or an interference filter, for example an optical polychroic interference filter, as a result of which it is possible to select the emitted fluorescence radiation vis-à-vis the excitation radiation.

Particularly preferably, the filters with the first, second and third filter characteristic are embodied as fluorescence filters for different fluorescence modes in each case. What this can achieve is that the filter interchange apparatus can facilitate the observation of three different fluorescence modes and consequently a particularly comprehensive distinction of different tissue types or of normal, diseased and necrotic tissue.

By way of example, for observing and recording the fluorescence of indocyanine green (ICG), one of the fluorescence filters can have a high transmission in a wavelength range from approximately 800 nm to 950 nm, in which the fluorescence light of the ICG fluorescence is emitted, and can largely block in a wavelength range around 785 nm, in which range an excitation radiation of the ICG fluorescence is usually located. Further, the filter can have a high transmission in a wavelength range from approximately 400 nm to 660 nm. What this can render achievable is that it is possible to observe not only the ICG fluorescence but also in white light using the fluorescence filter. To separate the white light from the ICG fluorescence radiation, a dichroic beam splitter can be provided downstream in each of the two beam paths, as a result of which radiation in a range from 400 nm to 660 nm can be guided to a first image recorder assigned to the respective stereo channel and the fluorescence radiation can be guided to a second image recorder assigned to the relevant stereo channel.

A further fluorescence filter can have a transmissivity for fluorescence light in a wavelength range from approximately 500 nm to 600 nm and act as a band-elimination filter in a wavelength range of the corresponding fluorescence excitation radiation, in particular at 405 nm; as a result, it is possible to observe the emitted fluorescence of protoporphyrin IX (PPIX) from accumulated 5-ALA dye, which is also referred to as PDD (photodynamic diagnosis) fluorescence. In the process, the autofluorescence of human or animal tissue can be excited at the same time, wherein the filter can additionally be transmissive in a wavelength range from approximately 410 to 600 nm for the purposes of observing the autofluorescence radiation. Here, too, a downstream dichroic beam splitter can be provided for the separate observation of the PPIX and the autofluorescence radiation.

In order to observe the fluorescence of fluorescein, which is advantageous for the identification of blood vessels in a tissue, for example, a further one of the fluorescence filters can have a high transmissivity in a wavelength range from approximately 500 nm to 600 nm and otherwise have a low transmission or act as a band-elimination filter.

According to a preferred embodiment of the invention, the second filter wheel is drivable by motor for rotation purposes. As a result of the drive of the second filter wheel being a motor drive, it is possible to simplify the operation and/or an automated filter change can be realized, which might be controlled by a control device, for example. In particular, this allows a quick and precise approach of specified filter swivel positions.

Preferably, the second filter wheel of the filter interchange apparatus is substantially drivable at its outer circumference. Here, the drive can act on an outer circumferential surface or a gear rim arranged thereon, or else on an end face or a circumferential edge of the disk of the filter wheel. As a result of the second filter wheel being driven by way of a surface situated on the outside, it is possible to improve the accuracy of the rotational movement. Moreover, it is possible to avoid having to arrange a drive in or between the two beam paths, which would increase the spatial requirement of the filter interchange apparatus or reduce the optical quality of the image representations. In particular, it is also possible to avoid a central, rotating and driven rotation axle, as a result of which, for example, play in and/or jamming of one of the filter wheels could influence the rotation of the other filter wheels.

Particularly preferably, the second filter wheel is drivable at its outer circumference by means of a motor drive, in particular by means of a motor driven pinion, which engages in a gear rim that extends over at least some of the outer circumference of the filter wheel, for example over 180°. Firstly, this can facilitate an automatic, secure and precise rotational movement of the second filter wheel. Secondly, as a result of the motor drive being arranged externally on the second filter wheel, it can easily be replaced in the case of an outage or a necessary replacement without the filter wheels having to be disassembled from the common axle.

According to a preferred embodiment, the filter interchange apparatus comprises a position identifying device for determining a respective rotational position of at least one of the filter wheels, preferably of the first and third filter wheel, particularly preferably of all filter wheels. In particular, the position identifying device is embodied to detect the reaching or not reaching of a respectively specified rotational position of the respective filter wheel. This may render determinable whether a filter wheel is still rotating during a filter change and has yet to arrive at a respective rotational position or when a rotation for swiveling one or more filters in or out has been completed. Furthermore, it may be clearly identifiable which filter is or which filters of the same type are currently swiveled into the beam paths and consequently which fluorescence mode is being recorded, for example. Furthermore, this may render an error state detectable, for instance a rotation of one or more of the filter wheels that has not been carried out or that has not been carried out in a manner sufficient for a filter change, for example triggered by jamming when moving the filter wheels. This can increase the safety when carrying out an operation with the optical observation instrument. To this end, the filter interchange apparatus or the optical observation instrument can comprise a control device or can be connectable to the latter, said control device being set up in such a way that it is possible to deduce a rotational movement being carried out or an error state from signals of the position identifying device.

Preferably, a position identifying device comprises a photoelectric sensor or a plurality of photoelectric sensors and the filter wheel has or a plurality of the filter wheels each have an associated flag. In particular, such a photoelectric sensor is an optoelectronic system which identifies the interruption of a light beam and indicates and/or outputs this as an electrical signal. Here, the respective flag can move into the photoelectric sensor by a rotation of the relevant filter wheel and, as a result, interrupt a light beam of the photoelectric sensor, as a result of which the relevant rotational position of the filter wheel is detected. In addition or as an alternative to a flag, one or more of the filter wheels can each have a cutout on the outer circumference such that one of the three filters is in each case captured by one of the photoelectric sensors. Preferably, the position identifying device comprises three photoelectric sensors, which each detect at least one flag or a cutout of one of the three filter wheels. Consequently, the rotational positions of the filter wheels can be detected in contactless fashion by means of one or more photoelectric sensors.

Preferably, the filter interchange apparatus comprises a mechanical stop device or a plurality of mechanical stop devices, up to which the first, second and/or third filter wheel is or are rotatable. In particular, the one or more stop devices can be embodied to set a final and/or initial position of a rotation of a respective filter wheel or to limit an angle range within which the filter wheel can rotate. This can improve the accuracy and reliability of the filter change.

In a particularly preferred manner, a position identifying device comprising at least one photoelectric sensor can be provided in addition to a stop device, wherein at least one of the filter wheels comprises an associated flag, the flag simultaneously serving as a stop lever of the stop device. Here, the stop devices can be embodied in such a way that a respective stop lever strikes a respective stop pin of the mechanical stop device when entering a photoelectric sensor or after passing the corresponding photoelectric sensor. This can facilitate a particularly simple structure.

By way of example, provision can be made for the second filter wheel to have a semicircular cutout or a diameter that is larger on one semicircle, which larger diameter can also be realized, for example, by the gear rim arranged on the outer circumference, while the first filter wheel and the third filter wheel each have, offset, a stop lever as a flag. The positions of the three filter wheels are monitored by three photoelectric sensors, which are arranged on the outer circumference of the filter wheels. Here, a first photoelectric sensor registers when the stop lever of the first filter wheel has reached its stop and a third photoelectric sensor registers when the stop lever of the third filter wheel has reached its stop. A second photoelectric sensor registers the cutout of the second filter wheel. Thus, for example, a first filter position can be detected by virtue of the first photoelectric sensor registering the stop lever of the first filter wheel and the central photoelectric sensor registering the missing cutout of the second filter wheel, a second filter position can be detected by virtue of the first and the second photoelectric sensor respectively registering the stop lever of the first filter wheel and the third filter wheel and the central photoelectric sensor registering the cutout of the second filter wheel, and a third filter position can be detected by virtue of the third photoelectric sensor registering the stop lever of the third filter wheel and the central photoelectric sensor registering the missing cutout of the second filter wheel. The filter interchange apparatus or the optical observation instrument can comprise a control device or can be connectable to the latter, said control device being set up in such a way that it is possible to deduce the positions of the filter wheels from the signals of the photoelectric sensors. As a result, it is possible to ensure a reliable, redundant position identification of the filter wheels.

In an additional aspect of the invention, the object is achieved by an optical observation instrument, in particular a stereoscopic observation instrument, for example a stereo video endoscope, a stereo exoscope or a stereo surgical microscope, having two beam paths, wherein the optical observation instrument comprises a filter interchange apparatus which is embodied as described above. Incidentally, the optical observation instrument can be embodied as described in the German patent application of the same applicant, entitled "Optisches Beobachtungsinstrument sowie Verfahren zum Erzeugen eines Stereobilds eines Objektfelds" [Optical observation instrument and method for generating a stereo image of an object field], which was filed on the same day as the present application and is incorporated herein by reference in its entirety.

In particular, the filter interchange apparatus is embodied to respectively introduce two filters of the same type into the two beam paths or remove said filters therefrom. The optical observation instrument can comprise two or more image sensors, for example four image sensors for a stereoscopic fluorescence recording and a stereoscopic white light recording. The optical observation instrument can particularly preferably be embodied for observing three different fluorescence modes and observations in white light. Further, the optical observation instrument can comprise an illumination optical unit for illuminating an object field with illumination radiation, in particular fluorescence excitation radiation, and can comprise a corresponding light source or can be connectable to the latter for this. Further, the optical observation instrument can comprise a control device or can be connectable to the latter, said control device being set up to control a motor-driven rotation of the second filter wheel and to identify a respective position of the filter wheels or an error state by means of the signals from a position identifying device.

Consequently, a stereoscopic observation instrument is provided, in which the filter interchange apparatus facilitates a quick and reliable interchange of three different filters, in particular fluorescence filters, and consequently the observation of three fluorescence modes and, additionally, white light while requiring very little installation space. Consequently, a very differentiated observation and recording of tissue is facilitated by means of the stereoscopic observation instrument.

According to a further aspect of the invention, a method for changing a filter of an optical observation instrument which has two beam paths and which comprises a filter interchange apparatus embodied as described above, in particular for changing the same type of filters into both beam paths in each case, comprises the following steps for a first filter change:

driving the second filter wheel through an adjustment angle in a first direction of rotation from an initial position of the second filter wheel for rotation about the common axle, entraining the first filter wheel through the adjustment angle from an initial position of the first filter wheel by means of the first entrainment device for rotation in the first direction of rotation, leaving the third filter wheel standing in an initial position of the third filter wheel.

Further, the following steps can be implemented for a further change of the filters in both beam paths:

driving the second filter wheel through twice the adjustment angle in a second direction of rotation, opposite to the first, for rotation about the common axle, restoring the first filter wheel to the initial position of the first filter wheel by spring force, entraining the third filter wheel through the adjustment angle from the initial position of the third filter wheel for rotation in the second direction of rotation.

In particular, the adjustment angle can be approximately 90°, wherein two filters of the same type and two free optical passages are preferably arranged in each of the first, the second and the third filter wheel, wherein the two filters and two free optical passages can lie opposite one another in each case.

It is self-evident that the features mentioned above and the features yet to be discussed below may be used not only in the respectively specified combination but also in other combinations or individually without departing from the scope of the present invention.

BRIEF DESCRIPTION OF THE DRAWINGS

Further aspects of the invention arise from the following description of a preferred exemplary embodiment and the attached drawing. In detail:

FIG. 8 shows a schematic plan view of three different filter arrangements corresponding to the illustration in FIG. 2; and FIG. 9 shows a schematic plan view, as seen in the beam direction, of the filter interchange apparatus in two intermediate positions of the filter wheels.

DETAILED DESCRIPTION

Figure 1:
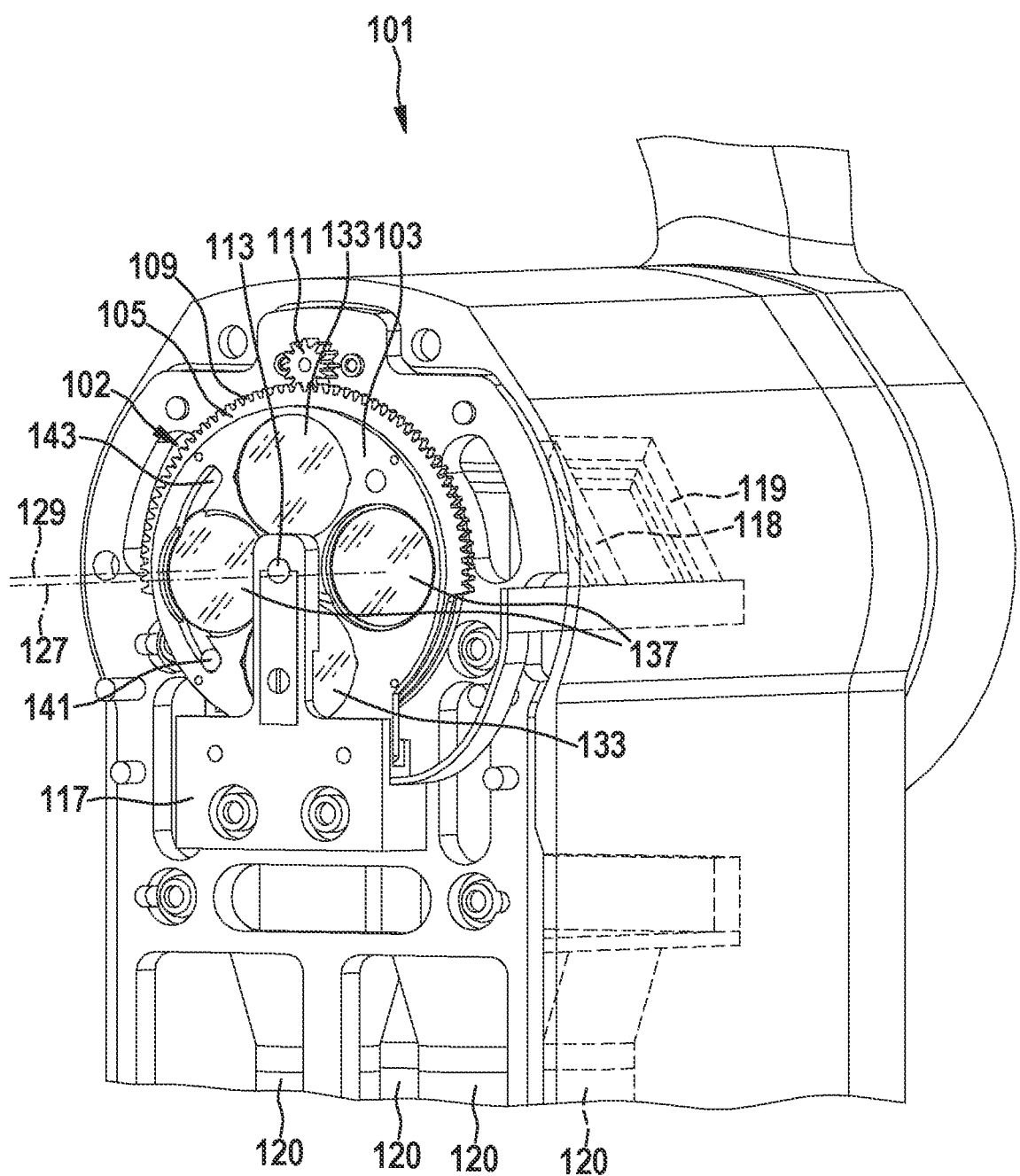
FIG. 1 shows a sectional illustration of a stereo surgical microscope having a filter interchange apparatus according to an exemplary embodiment of the invention.

As illustrated in FIG. 1 in exemplary fashion, a stereo surgical microscope 101, which has two beam paths, comprises a filter interchange apparatus (filter interchanger 102). The two beam paths are the beam paths of the two stereo channels of the stereo surgical microscope 101 and represent observation beam paths for the stereoscopic observation of tissue in three different fluorescence modes and in white light. FIG. 1 shows part of the inner structure of a rotatable optical unit of the stereo surgical microscope, without a zoom assembly, which is arranged on the distal side of the illustrated sectional plane, and without the housing of the optical unit. In respect of the structure and the function of a suitable optical observation instrument, reference is made to the German patent application of the same applicant, entitled "Optisches Beobachtungsinstrument sowie Verfahren zum Erzeugen eines Stereobilds eines Objektfelds" [Optical observation instrument and method for generating a stereo image of an object field], which was filed on the same day as the present application.

The filter interchanger 102 comprises a first filter wheel 103, a second filter wheel 105 and a third filter wheel 107 arranged therebehind. The filter wheels 103, 105 and 107 are rotatably mounted on a stationary rotation axle 113, wherein the rotation axle 113 is fastened at one end by means of a holder 117. The first filter wheel 103, the second filter wheel 105 and the third filter wheel 107 are arranged in succession, wherein all three filter wheels 103, 105, 107 each have a central bore 139 (see below), by means of which the filter wheels 103, 105 and 107 are connected to the stationary rotation axle 113.

In the initial position shown in FIG. 1, the first filter wheel 103 comprises two filters 133, vertically opposite one another, for observing the PPIX (PDD) fluorescence (PPIX filter 133) and two free optical passages 137, horizontally opposite one another, which are each embodied as openings with a similar width as the filters 133. The two filters of the second filter wheel 105 are visible (see below) through the free optical passages of the first filter wheel 103. On one half, the second filter wheel 105 is surrounded by a gear rim 109 on an outer circumference, said gear rim engaging in a pinion 111 that is driven by an electric motor (see below). Moreover, the second filter wheel 105 comprises a first entrainment pin 141, which engages in a slot 143 of the first filter wheel 103. As seen from the rotation axle 113, the slot 143 extends over approximately a quarter circle.

In the illustration of FIG. 1, the two beam paths of the stereo surgical microscope are offset horizontally with respect to one another and extend parallel to one another through the horizontal free optical passages 137 of the first filter wheel 103 and into the plane of the drawing. The optical axes 127, 129 of the two beam paths are indicated in FIG. 1. The beam paths are afocal in the region of the filter interchanger 102. Arranged downstream in the beam paths in each case are a dichroic beam splitter 118 and further a deflection mirror 119, by means of which the radiation passing through the filter interchanger 102 is spectrally split and deflected in the direction of imaging optical units 120, which in each case generate a corresponding image on two correspondingly assigned electronic image recorders (not shown in detail in FIG. 1).

Figure 2:
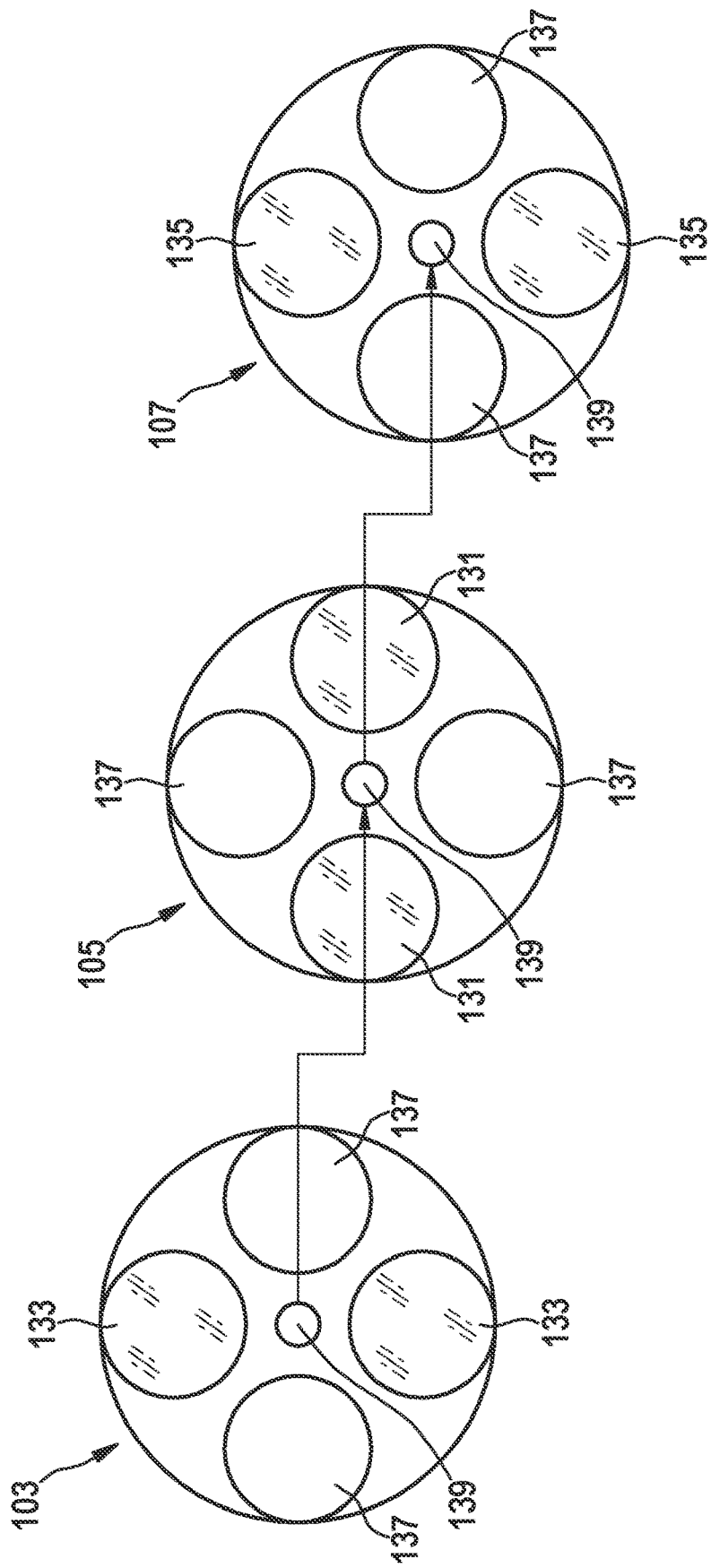
FIG. 2 shows a schematic illustration of the arrangement of the filters in the three filter wheels according to the exemplary embodiment of the invention.

FIG. 2 illustrates, in a schematic form, the arrangement of the filters in the three filter wheels 103, 105, 107 in a respective initial position. As mentioned, the first filter wheel 103 in the initial position has two PPIX filters 133 lying vertically opposite one another and two free optical passages 137 lying horizontally opposite one another. The second filter wheel 105 has two free optical passages 137 lying vertically opposite one another and two filters 131 for observing ICG fluorescence (ICG filters 131) lying horizontally opposite one another and the third filter wheel 107 has two filters 135 for observing fluorescein fluorescence (fluorescein filter 135) lying vertically opposite one another and two optical passages 137 lying horizontally opposite one another.

By rotating the second filter wheel 105 by way of the gear drive by means of the pinion 111, which moves the gear rim 109, in a direction of rotation 115 of the second filter wheel 105 or counter to the direction of rotation 115, it is possible to realize three filter arrangements on account of entraining the first filter wheel 103 or of the third filter wheel 107 by way of the respective entrainment pin 141 and leaving the third filter wheel 107 or the first filter wheel 103 standing. These are shown schematically in FIG. 3 in a direction counter to the beam direction, i.e., in accordance with the view in FIGS. 6 to 9 (see below).

In the initial position shown in FIG. 2, the two ICG filters 131 of the second filter wheel 105 are in the two beam paths, while the first and the second filter wheel 103, 105 each lie with their free optical passages 137 in the two stereo beam paths of the stereo surgical microscope 101. The filters 131 in each case cover approximately the entire cross section of the relevant beam path. The penetration points of the optical axes 127, 129 through the respectively swiveled-in filters are marked in FIG. 3. Accordingly and respectively in succession, a PPIX filter 133 of the first filter wheel 103 and a fluorescein filter 135 of the third filter wheel 107 are situated vertically opposite one another outside of the beam paths. This filter arrangement (second filter arrangement 123) is illustrated in the central image representation in FIG. 3. As a result, the fluorescence radiation of the observed tissue region generated by ICG is observable, as is the tissue region in white light.

Figure 3:
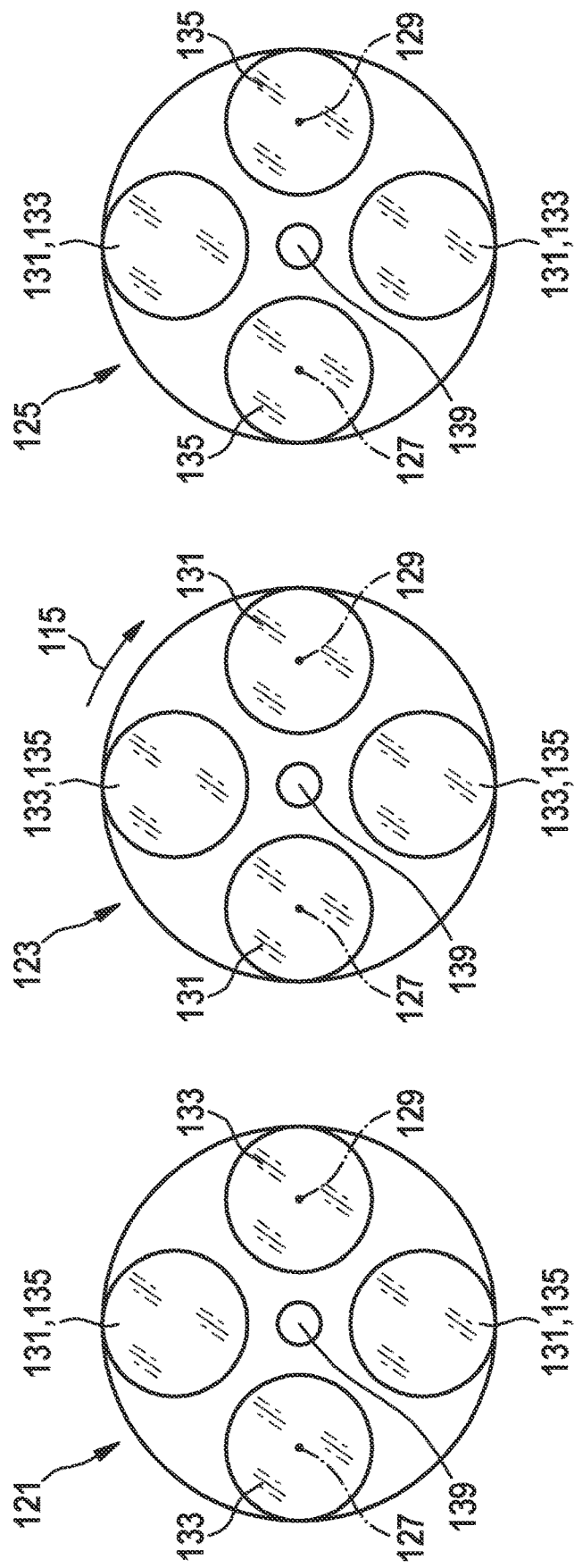
FIG. 3 shows a schematic illustration of three filter arrangements.

As a result of a 90° rotation of the second filter wheel 105 in the direction of rotation 115 and an entrainment of the first filter wheel 103 while leaving the third filter wheel 107 standing, a PPIX filter 133 is arranged in the first stereo beam path and a second PPIX filter 133 is arranged in the second beam path of the stereo surgical microscope 101, in each case lying horizontally opposite one another, in the first filter arrangement 121 which is illustrated in the left image representation of FIG. 3. As a result, the fluorescence of PPIX (PDD fluorescence) is observable and recordable; likewise, the autofluorescence of the observed tissue region may be observable under certain circumstances. Outside of the two beam paths and in succession, there respectively are vertically opposite to one another an ICG filter 131 of the second filter wheel 105 and a fluorescein filter 135 of the third filter wheel 107.

As a result of a rotation of the second filter wheel 105 through 90° counter to the direction of rotation 115 following the return into the initial position, while entraining the third filter wheel 107 and while leaving the first filter wheel 103 standing, a third filter arrangement 125 (right image representation of FIG. 3) is reached, in which a fluorescein filter 135 of the third filter wheel 107 is respectively switched into the first beam path and into the second beam path in horizontally opposing fashion such that the fluorescence emitted by fluorescein is observable while, lying vertically opposite one another and outside of the beam paths, respectively one ICG filter 131 and one PPIX filter 133 are arranged in succession.

Figure 4:
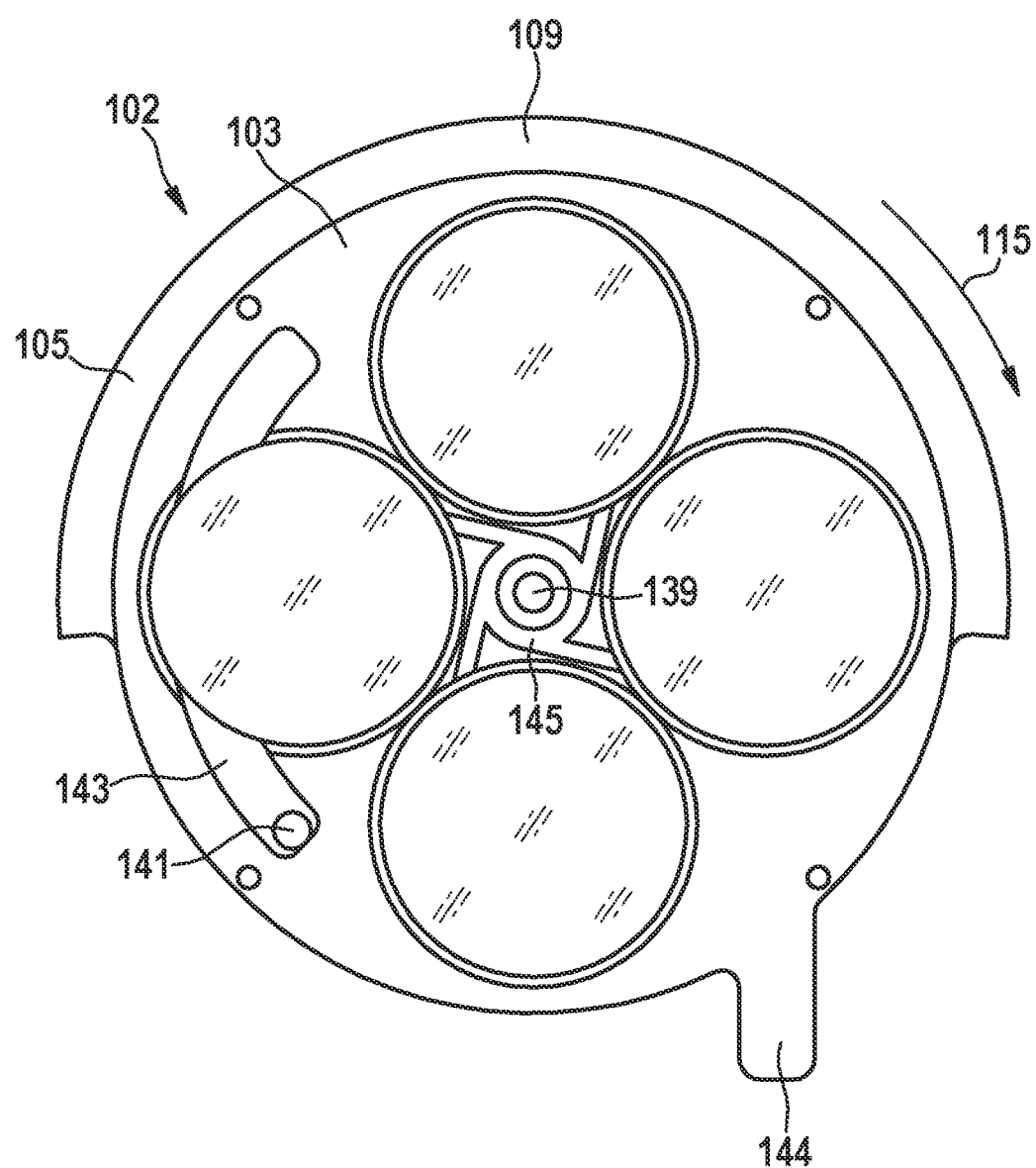
FIG. 4 shows a schematic illustration of the arrangement of the filter wheels of the filter interchange apparatus, as a plan view seen in the beam direction.

As shown in FIG. 4 in the beam direction in an axial plan view of the approximately circular disk forming the first filter wheel 103, the second filter wheel 105 has the gear rim 109 running through approximately 180° along its circumference, with the teeth not being illustrated for reasons of simplicity in FIG. 4 and the subsequent figures. The second filter wheel 105 is driven at the semicircular gear rim 109 by way of the pinion 111 (see below). The disk of the first filter wheel 103 is interrupted by the quarter circle-shaped slot 143, through which the second filter wheel 105 is visible in FIG. 4 and into which the first entrainment pin 141 of the second filter wheel 105 engages. Moreover, the first filter wheel 103 comprises a restoring spring 145 about the central bore 139 and hence about the stationary rotation axle 113, said restoring spring being provided to restore the first filter wheel 103 to the initial position. The third filter wheel 107, not visible in FIG. 4, has a configuration corresponding to the first filter wheel 103. Moreover, the first filter wheel 103 comprises a stop lever 144 for abutting against a stop pin 149 and for engaging with a photoelectric sensor 147 (see below). The semicircular gear rim 109, which increases the diameter of the second filter wheel 105 on one half, is likewise used for detection by means of a photoelectric sensor 147.

In FIGS. 5 to 9, the filter interchanger 102 or the filter wheels are illustrated in reverse to the state in FIG. 1 and FIG. 4; i.e., for example, the pinion 111 arranged above the second filter wheel 105 in FIG. 1 is illustrated below the second filter wheel in FIGS. 5 to 9.

Figure 5:
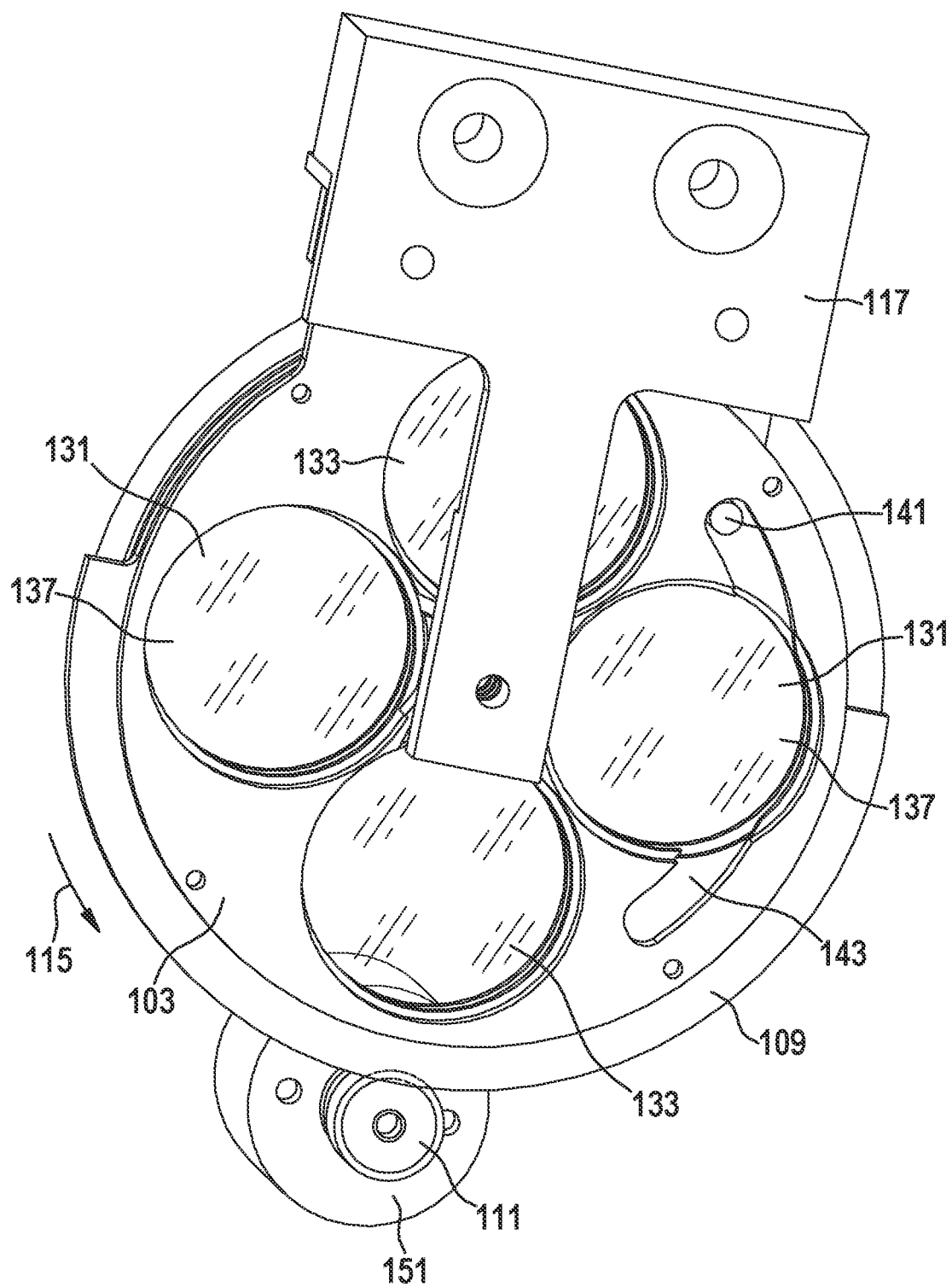
FIG. 5 shows the filter interchange apparatus according to FIG. 1, as seen in an oblique view in the beam direction.

In FIG. 5, the filter interchanger 102 is illustrated in a view seen obliquely in the beam direction; this view approximately corresponds to the view in FIG. 1, although it is illustrated reversely.

As shown in FIG. 5, the first filter wheel 103 has the quarter circle-shaped slot 143, in which the first entrainment pin 141 engages. The slot 143 is penetrated by one of the two free optical passages 137, arranged opposite one another, of the first filter wheel 103. In this rotational position, which corresponds to the first filter arrangement 121 (see FIG. 3), the PPIX filters 133 of the first filter wheel 103 are arranged vertically opposite one another and consequently outside of the beam paths. The ICG filters 131 of the second filter wheel 105 are visible through the free optical passages 137.

Further, FIG. 5 indicates that the filter interchanger 102 comprises an electric motor 151, which engages in the gear rim 109 of the second filter wheel 105 by means of the pinion 111, with the teeth not being illustrated. Only the second filter wheel 105 is driven directly, while the first filter wheel 103 and the third filter wheel 107 are only entrained by way of the first and second entrainment pin 141, respectively, in accordance with the embodiment of the respective slots 143.

Figure 6:
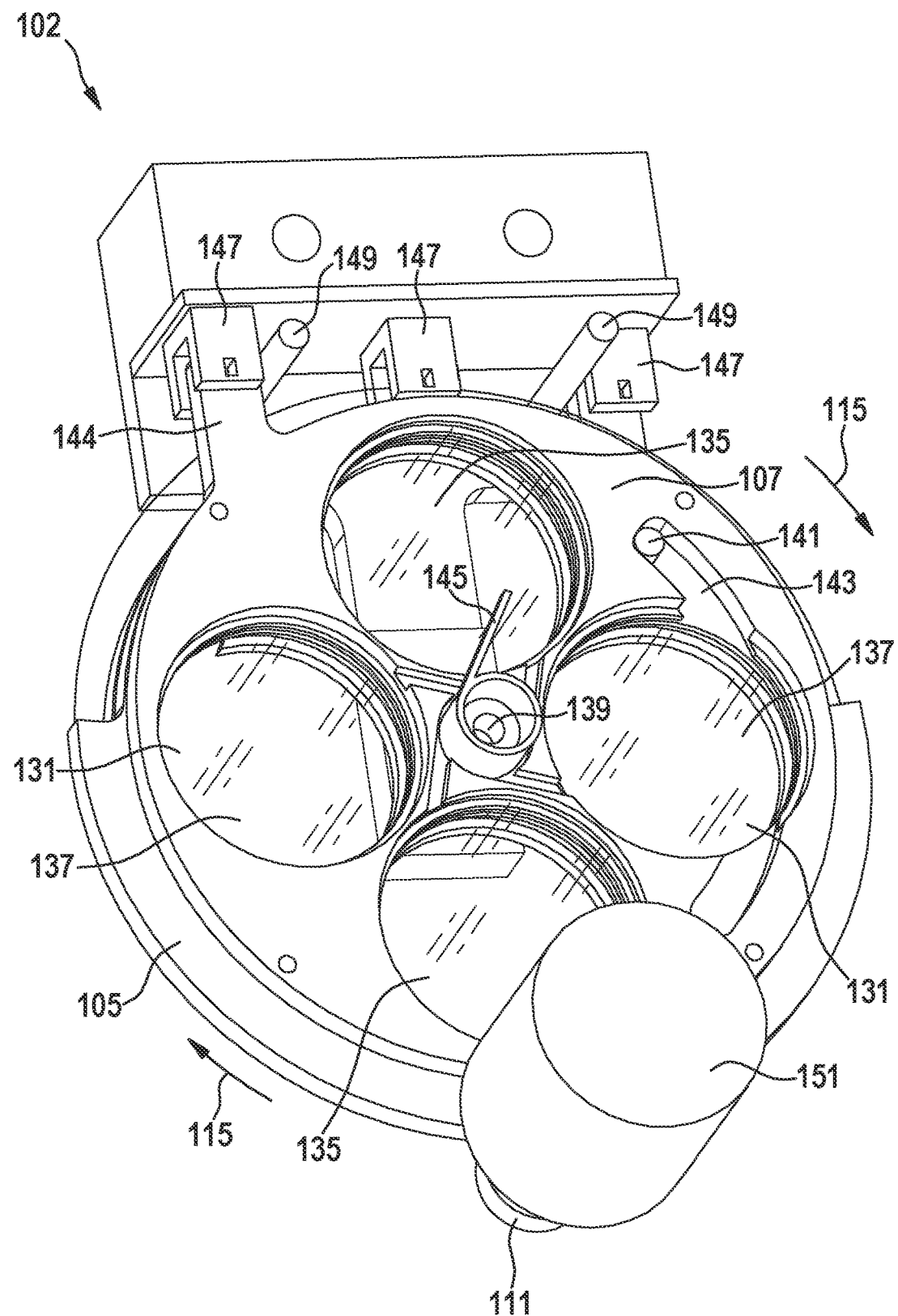
FIG. 6 shows the filter interchange apparatus according to FIG. 1, as seen in an oblique view counter to the beam direction.

FIG. 6 illustrates the filter interchanger 102 in an oblique view from behind (cf. FIG. 1), i.e., substantially counter to the beam direction. Here, the third filter wheel 107 and the gear rim 109 of the second filter wheel 105 are visible. In comparison with the first filter wheel 103 shown previously, the third filter wheel 107 correspondingly has a slot 143, in which the second entrainment pin 141 of the second filter wheel 105 engages. The third filter wheel 107 has the bore 139 centrally and a restoring spring 145 tensioned thereabout. Moreover, the third filter wheel 107 in each case has, opposite one another, two free optical passages 137 and two fluorescein filters 135, wherein the fluorescein filters 135 are arranged vertically opposite one another and hence outside of the beam paths in the rotational position shown in FIG. 6, which corresponds to the second filter arrangement 123 (see FIG. 3). The filters 131 of the second filter wheel 105 are visible through the optical passages 137.

As shown in FIG. 6, a stop lever 144 of the third filter wheel 107 is, in this rotational position, situated in the detection region of the first photoelectric sensor 147 and simultaneously abuts against the stop pin 149. The centrally arranged photoelectric sensor 147 serves to detect a position of the second filter wheel 105 and the photoelectric sensor 147 arranged to the right in FIG. 5 serves to detect a position of the first filter wheel 103.

Proceeding from the initial position shown in FIGS. 5 and 6, which corresponds to the second filter arrangement 123 (see FIG. 3), the first filter wheel 103 is entrained by the first entrainment pin 141 in the case of a rotation of the second filter wheel 105 in the direction of rotation 115 (see FIG. 5) while the third filter wheel 107 is left standing since the second entrainment pin 141 can move in the slot 143 of the third filter wheel 107 (see FIG. 5). The first filter arrangement 121 (see FIG. 3) is reached by a rotation through 90°. When the second filter wheel 105 is rotated back into the initial position, the first filter wheel 103 is returned into its initial position by the restoring spring 145 of the first filter wheel 103, wherein a stop lever 144 of the first filter wheel 103 drives into the photoelectric sensor 147 (illustrated to the right in FIG. 6) and simultaneously abuts against the corresponding stop pin 149.

Conversely, proceeding from the second filter arrangement 123, the third filter wheel 107 is entrained by the second entrainment pin 141 in the case of a rotation of the second filter wheel 105 counter to the direction of rotation 115 (see FIG. 6) while the first filter wheel 103 is left standing since the first entrainment pin 141 can move in the slot 143 of the third filter wheel 107 (see FIG. 5). As a result, the third filter arrangement 125 (see FIG. 3) is reached. Subsequently, the third filter wheel 107 can be returned into its initial position by the restoring spring 145, wherein the stop lever 144 of the third filter wheel 107 drives into the photoelectric sensor 147 (illustrated to the left in FIG. 6) and simultaneously abuts against the corresponding stop pin 149.

Figure 7:
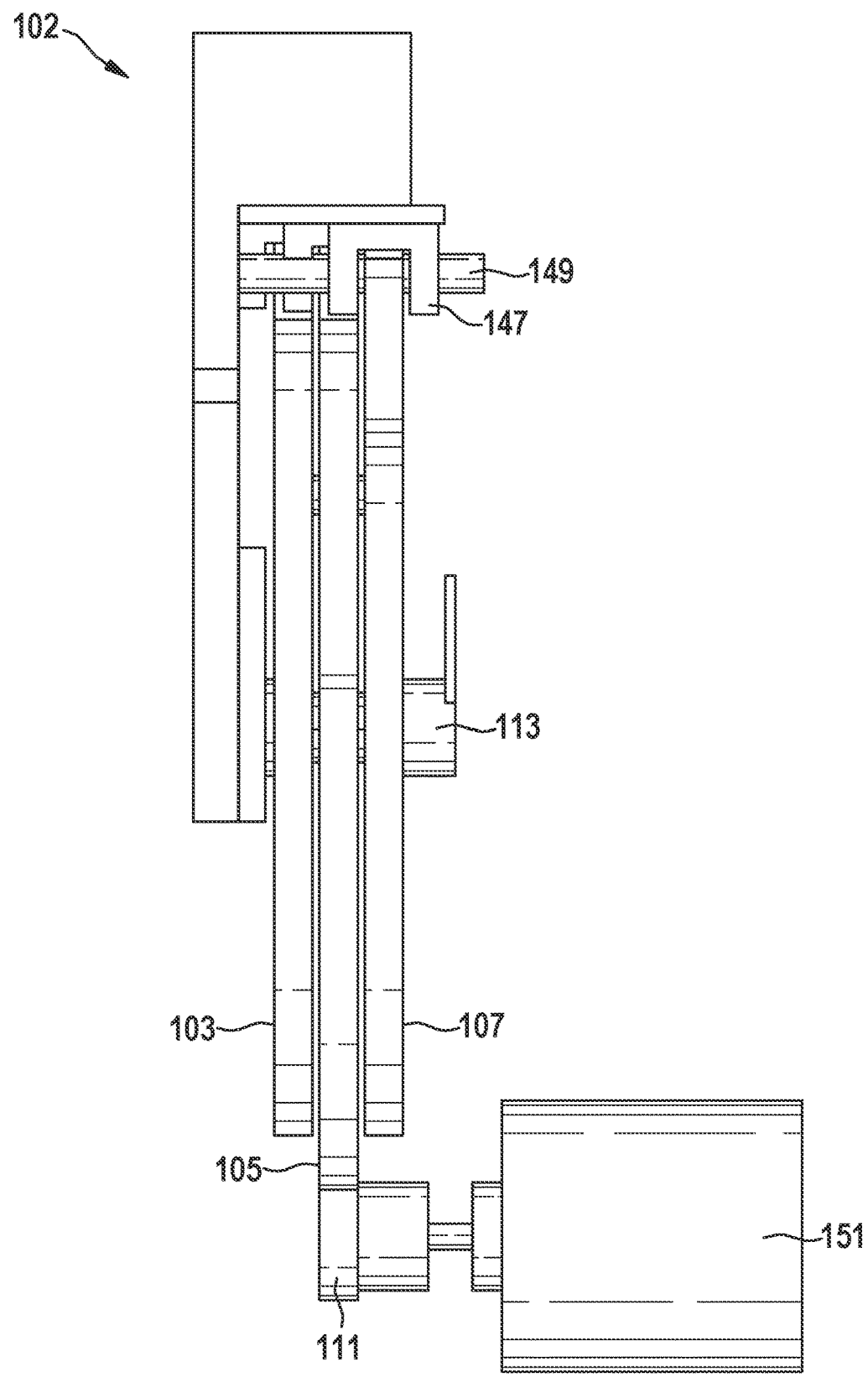
FIG. 7 shows a side view of the filter interchange apparatus.

FIG. 7 illustrates the filter interchanger 102 in a side view. As can be identified in FIG. 7, the filter wheels 103, 105, 107 are arranged with little distance from one another such that the filter interchanger 102 overall only has a slightly greater spatial requirement than a single one of the filter wheels 103, 105, 107 and consequently can have a very compact embodiment.

FIG. 8 shows three different filter arrangements, which correspond to the filter arrangements 121, 123, 125 in FIG. 3, likewise seen counter to the beam direction. Here, it is possible to identify that the left and the right photoelectric sensors 147 are interrupted in the second filter arrangement 123, which constitutes the initial position. The left-hand and central photoelectric sensors 147 are interrupted in the first filter arrangement 121 while the central and the right-hand photoelectric sensors 147 are interrupted in the third filter arrangement 125. Consequently, a respective filter position can be ascertained from the signals of the photoelectric sensors 147.

Further, as shown in the left-hand image representation in FIG. 9, the assumption can be made that the second filter wheel 105 is still in motion and has not reached a corresponding end position in those cases where only the left-hand (or, accordingly, only the right-hand) photoelectric sensor 147 is interrupted. By contrast, in accordance with the right-hand image representation in FIG. 9, an error state is assumed when none of the photoelectric sensors are interrupted, in which error state, for example, the first or the third filter wheel 103, 107 is jammed and can no longer be returned to its initial position by the respective restoring spring 145. Consequently, the signals of the photoelectric sensors 147 allow a deduction as to whether a rotational movement has not yet been completed and, optionally, as to whether an error state of the filter interchanger 102 is present.

Consequently, a stereo surgical microscope 101 with a very compact filter interchanger 102 is realized, which filter interchanger realizes a very fast interchange between ICG filters 131, PPIX filters 133 and fluorescein filters 135 and consequently between the three fluorescence modes, and which consequently facilitates an optimal differentiation of a tissue to be examined.

Not all reference signs have been presented in all figures for reasons of clarity. Reference signs not explained in relation to one figure have the same meaning as in the other figures.

LIST OF REFERENCE SIGNS

101 Stereo surgical microscope
102 Filter interchanger
103 First filter wheel
105 Second filter wheel
107 Third filter wheel
109 Gear rim
111 Pinion
113 Rotation axle
115 Direction of rotation
117 Holder
118 Beam splitter
119 Deflection mirror
120 Imaging optical unit
121 First filter arrangement
123 Second filter arrangement
125 Third filter arrangement
127 Optical axis
129 Optical axis
131 ICG filter
133 PPIX filter
135 Fluorescein filter
137 Free optical passage
139 Bore
141 Entrainment pin
143 Slot
144 Stop lever
145 Restoring spring
147 Photoelectric sensor
149 Stop pin
151 Electric motor

The invention claimed is:

1. A filter interchange apparatus fore optical observation instrument having two beam paths comprising:
a common axle,
a first filter wheel,
a second filter wheel, and
a third filter wheel, wherein the filter wheels are arranged in succession along the common axle and are rotatable about the common axle and relative to one another, wherein each filter wheel comprises at least one filter and at least one free optical passage such that a filter or a free optical passage of each filter wheel is introducible into each of the two beam paths and wherein the second filter wheel is drivable and the first filter wheel is coupled to the second filter wheel via a first entrainment element and the third filter wheel is coupled to the second filter wheel via a second entrainment element.

2. The filter interchange apparatus as claimed in claim 1, wherein the second filter wheel is arranged between the first filter wheel and the third filter wheel.

3. The filter interchange apparatus as claimed in claim 1, wherein the first filter wheel is coupled to the second filter wheel via the first entrainment element in such a way that, proceeding from an initial position, the first filter wheel is entrained in the case of a rotation of the second filter wheel in a first direction of rotation and remains stationary in a second direction of rotation.

4. The filter interchange apparatus as claimed in claim 3, wherein the first and/or the second entrainment element is an entrainment pin of the second filter wheel, which engages in a cutout of the first filter wheel or a cutout of the third filter wheel and within which cutout the entrainment pin is able to freewheel within a freewheel angle range.

5. The filter interchange apparatus as claimed in claim 4, wherein the cutout of the first filter wheel and/or of the third filter wheel is a ring segment-shaped groove or as a ring segment-shaped slot.

6. The filter interchange apparatus as claimed in claim 1, wherein the third filter wheel is coupled to the second filter wheel via the second entrainment element in such a way that, proceeding from an initial position, the third filter wheel remains stationary in the case of a rotation of the second filter wheel in a first direction of rotation and entrained in a second direction of rotation.

7. The filter interchange apparatus as claimed in claim 1, wherein one or more of the first filter wheel and the third filter wheel comprises a restoring device, or a restoring spring, configured to restore the respective filter wheel to an initial position.

8. The filter interchange apparatus as claimed in claim 1, wherein the first filter wheel comprises two filters with a first filter characteristic and two free optical passages, the second filter wheel comprises two filters with a second filter characteristic and two free optical passages and/or the third filter wheel comprises two filters with a third filter characteristic and two free optical passages.

9. The filter interchange apparatus as claimed in claim 1, wherein the first filter wheel comprises two filters with a first filter characteristic lying opposite one another and two free optical passages lying opposite one another, the second filter wheel comprises two filters with a second filter characteristic lying opposite one another and two free optical passages lying opposite one another and/or the third filter wheel comprises two filters with a third filter characteristic lying opposite one another and two free optical passages lying opposite one another.

10. The filter interchange apparatus as claimed in claim 1, wherein at least one of the filters is a fluorescence filter, wherein the filters with the first, second and/or third filter characteristic are fluorescence filters.

11. The filter interchange apparatus as claimed in claim 1, wherein the second filter wheel is drivable by a motor.

12. The filter interchange apparatus as claimed in claim 1, wherein the second filter wheel is drivable at its outer circumference by a gear rim which is arranged on an outer circumference of the second filter wheel and which meshes with a pinion.

13. The filter interchange apparatus as claimed in claim 1, wherein the filter interchange apparatus comprises a position identifying device configured to determine a respective rotational position of at least one of the filter wheels.

14. The filter interchange apparatus as claimed in claim 13, wherein the position identifying device comprises at least one photoelectric sensor and at least one of the filter wheels comprises an associated flag.

15. The filter interchange apparatus as claimed in claim 1, wherein the filter interchange apparatus comprises a mechanical stop device or a plurality of mechanical stop devices configured to restrict a rotation of the first filter wheel, of the second filter wheel and/or of the third filter wheel.

16. The filter interchange apparatus as claimed in claim 1, wherein the optical observation instrument is a stereoscopic observation instrument, a stereo video endoscope, a stereo exoscope or a stereo surgical microscope.

17. A method to change a filter of an optical observation instrument having two beam paths and comprising a filter interchange apparatus including a first filter wheel, a second filter wheel and a third filter wheel, wherein the filter wheels are arranged in succession along a common axle and are rotatable about the common axle and relative to one another, wherein each filter wheel comprises at least one filter and at least one free optical passage such that a filter or a free optical passage of each filter wheel is introducible into each of the two beam paths and wherein the second filter wheel is drivable and the first filter wheel is coupled to the second filter wheel via a first entrainment element and the third filter wheel is coupled to the second filter wheel via a second entrainment element, wherein, for a first filter change, the method comprises:
driving the second filter wheel through an adjustment angle in a first direction of rotation from an initial position of the second filter wheel for rotation about the common axle,
entraining the first filter wheel through the adjustment angle from an initial position of the first filter wheel by the first entrainment element for rotation in the first direction of rotation, and
maintaining the third filter wheel in an initial position of the third filter wheel,
and, for a further filter change the method comprises:
driving the second filter wheel through twice the adjustment angle in a second direction of rotation, opposite to the first, for rotation about the common axle,
restoring the first filter wheel to the initial position of the first filter wheel by spring force, and
entraining the third filter wheels through the adjustment angle from the initial position of the third filter wheel for rotation in the second direction of rotation.

18. The method of claim 17, wherein the optical observation instrument is a stereo video endoscope, a stereo exoscope or a stereo surgical microscope.

19. A filter interchange apparatus for an optical observation instrument having two beam paths comprising:
a common axle,
a first filter wheel,
a second filter wheel, and
a third filter wheel, wherein the filter wheels are arranged in succession along the common axle and are rotatable about the common axle and relative to one another, wherein each filter wheel comprises at least one filter and at least one free optical passage such that a filter or a free optical passage of each filter wheel is introducible into each of the two beam paths, and wherein only the second filter wheel is drivable by a drive, and the first filter wheel is coupled to the second filter wheel via a first entrainment element and the third filter wheel is coupled to the second filter wheel via a second entrainment element with the first filter wheel and the third filter wheel not being engaged by the drive.

* * * * *